United States Patent [19]  [11] 4,172,052
Foster  [45] Oct. 23, 1979

[54] CATALYST FOR PRODUCTION OF ETHYLENE DICHLORIDE

[75] Inventor: Robbie T. Foster, Corpus Christi, Tex.

[73] Assignee: PPG Industries, Inc., Pittsburgh, Pa.

[21] Appl. No.: 854,949

[22] Filed: Nov. 25, 1977

[51] Int. Cl.$^2$ .......................... B01J 27/06; B01J 29/06
[52] U.S. Cl. ............................... 252/442; 252/455 R; 260/659 A
[58] Field of Search .................. 252/442, 455 R; 260/659 A

[56] References Cited

U.S. PATENT DOCUMENTS

| | | | |
|---|---|---|---|
| 3,214,481 | 10/1965 | Heinemann et al. | 260/659 A |
| 3,232,889 | 1/1966 | Bellis | 252/441 |
| 3,378,597 | 4/1968 | Dehn et al. | 260/652 |
| 3,420,901 | 1/1969 | Schulz | 260/659 A |
| 3,427,359 | 2/1969 | Rectenwald et al. | 260/659 A |
| 3,649,698 | 3/1972 | Schmerling | 252/442 X |
| 3,691,098 | 9/1972 | Calcagno et al. | 252/442 X |
| 3,785,999 | 1/1974 | Derleth et al. | 252/442 X |

Primary Examiner—Carl Dees
Attorney, Agent, or Firm—Edward J. Whitfield

[57] ABSTRACT

Ethylene dichloride having a reduced chloral content is prepared by vapor phase oxychlorination of ethylene in the presence of a catalyst comprising aluminum halide and copper halide carried on a particulate support.

21 Claims, No Drawings

CATALYST FOR PRODUCTION OF ETHYLENE DICHLORIDE

BACKGROUND OF THE INVENTION

Ethylene dichloride (1,2-dichloroethane) may be produced by the oxychlorination of ethylene wherein ethylene, a chlorine source, and an oxygen source are contacted in the vapor phase in the presence of a catalyst. Typically, a gaseous mixture of ethylene, hydrogen chloride, and oxygen are reacted in the presence of a copper halide catalyst to produce a gaseous stream of ethylene dichloride. When ethylene is so oxychlorinated, satisfactorily high yields of ethylene dichloride may be obtained under moderate reaction conditions, however, the product typically contains objectionable amounts of chloral, i.e., in excess of about 0.2 percent by weight. Chloral, in addition to being classified as a pollutant, boils quite close to ethylene dichloride and is both difficult and costly to remove by, for example, distillation, to produce high purity ethylene dichloride.

One means of purifying chloral contaminated ethylene dichloride is disclosed in U.S. Pat. No. 3,378,597 wherein the oxychlorination product gas stream is condensed to form organic and inorganic liquid phases. The organic phase containing ethylene dichloride and chloral is separated from the inorganic phase and treated with aqueous sodium hydroxide to decompose the chloral to chloroform and sodium formate. However, both chloroform and sodium formate also pose a waste disposal problem and require additional treatment, e.g., bioxidation, before being discharged to a receiving stream.

SUMMARY OF THE INVENTION

In the production of ethylene dichloride by vapor phase oxychlorination of ethylene, chloral formation is suppressed by conducting the oxychlorination reaction in the presence of a catalyst comprising copper halide and aluminum halide carried on a particulate support.

DESCRIPTION OF THE INVENTION

The catalyst of the invention is prepared by treating the particulate support material with aqueous metal halide solution. The support material may be any commonly used catalyst carrier, e.g., silica, silica gel, alumina, diatomaceous earth, and the like. If the catalyst is to be used in a fluidized rather than a fixed bed, silica or high silica or alkali metal silicate content clay minerals are preferred support materials, some examples of which are bentonite, kaolite, illite and attapulgite clay minerals. Alumina or high alumina content clay materials, e.g., diaspore and bauxite clays, may be used; however, these have been found to be somewhat more friable and to have a higher attrition rate when used in a fluidized bed than the predominately silica or alkali metal silicate containing clays. Of the clay minerals, attapulgite is particularly preferred.

Copper halide and aluminum halide are selected from copper chloride, copper iodide, copper bromide, aluminum chloride, aluminum iodide and aluminum bromide. Copper chloride and aluminum chloride are preferred since they are more compatible with the chlorine containing compounds formed in the oxychlorination system and are more readily available.

The catalysts may contain alkali metal halide which serves to reduce volatilization of the catalytic actives, i.e., aluminum and copper halides, as well as to control burning under oxychlorination conditions. Preferred alkali metal halides are sodium chloride and potassium chloride.

The catalyst is preferably prepared by a two-step process. In the first step, the support material is thoroughly mixed with an aqueous aluminum halide solution. The resultant slurry is evaporated to dryness and the dried cake is pulverized and is thoroughly mixed, in the second step, with aqueous copper halide solution. The slurry is again evaporated to dryness and the dried cake is ground to the desired particle size. The alkali metal halide may be present in either the aluminum halide or the copper halide solution, preferably the latter. The catalyst may also be prepared in one step, i.e., by mixing the support material with a single aqueous solution containing aluminum halide, copper halide and optionally, alkali metal halide. It has been observed, however, that the "two-step" catalyst appears to be slightly better in reducing chloral formation than the one-step catalyst and appears to be somewhat less friable when used in a fluidized bed under oxychlorination reaction conditions, although a catalyst prepared by either method gives acceptable results.

The relative quantities of aluminum halide and copper halide used in the preparation of the catalyst are such that the aluminum content of the catalyst is from about 4 to 8 percent by weight, preferably from about 5 to 7 percent by weight and the copper content of the catalyst is from about 4 to 10 percent by weight, preferably from about 5 to 8 percent by weight based on the total weight of catalyst, i.e., combined weights of metal halides plus support material.

Alkali metal halide, if used in the catalyst formulation, is used in sufficient quantity such that the alkali metal content of the catalyst is from about 2 to 6 percent by weight, preferably from about 3 to 4 percent by weight alkali metal based on the total weight of catalyst, i.e., combined weights of aluminum and copper halides, alkali metal halide, and support material.

It is to be understood that what is meant by aluminum, copper and alkali metal halide content of the catalyst refers to that aluminum, copper and alkali metal content resulting from treating the support material with the respective halides, and does not include aluminum, copper and alkali metal inherently present in the support material.

Copper halide, particularly copper chloride, alone or in combination with alkali metal halide, particularly sodium or potassium chloride, is known to be effective in catalyzing the vapor phase oxychlorination of ethylene to ethylene dichloride with, however, the attendant disadvantage of producing a chloral-contaminated product. Copper chloride supported on alumina is also known and use of the same as a catalyst in the oxychlorination of ethylene to ethylene dichloride has been found to produce ethylene dichloride having a chloral content lower than that produced using copper chloride supported on, for example, attapulgite clay. However, under oxychlorination conditions, and particularly in a fluidized bed, copper chloride on alumina is too friable and has a very high attrition rate. When the copper chloride on alumina catalyst is modified according to the invention by the use of aluminum chloride, not only is chloral formation reduced even further but the alumina support is considerably less friable and has a considerably decreased rate of attrition.

Thus, the use of aluminum chloride in the preparation of the catalyst of the invention not only permits the production of low chloral content ethylene dichloride by the oxychlorination of ethylene but also improves the physical characteristics of the support materials, particularly alumina and high alumina content clay minerals and makes these support materials more suitable for use in fluidized bed reactors by reducing their friability and attrition rates.

In a typical practice of the invention, ethylene, hydrogen chloride, and oxygen gases are fed in known manner to a fluid reactor at a rate sufficient to maintain the catalyst bed in a fluidized condition without significant entrainment of catalyst particles in the product gas and to intimately contact the gaseous reactants with the fluid catalyst. Particle size of the catalyst is not particularly critical, although for fluid bed operation, catalyst particle size is typically in the range of 30 to 200 mesh (U.S. Sieve), preferably between 40 and 100 mesh. The reaction may be conducted over a wide range of temperature, for example, between 150° C. to 500° C., preferably between 250° C. and 350° C. Contact time between the gaseous reactants and the catalyst is typically not more than about two minutes and usually about 10 seconds. Depending on reaction conditions, conversion of ethylene to ethylene dichloride usually ranges from about 70 percent to substantially quantitative, and an ethylene dichloride crude having an ethylene dichloride content of from 97 percent to 99 percent may be obtained.

Of course, the vapor phase oxychlorination of ethylene to ethylene dichloride may be conducted using a fixed rather than a fluidized catalyst bed in known manner and under known process conditions.

The effectiveness of the catalyst of the invention in suppressing chloral formation in the vapor phase oxychlorination of ethylene to ethylene dichloride is illustrated by the following examples.

EXAMPLE 1

About 1500 grams of 30×60 mesh (U.S. Sieve) attapulgite clay were thoroughly mixed with an aqueous aluminum chloride solution prepared by dissolving about 669 grams of $AlCl_3.6H_2O$ in about 1500 milliliters of water. The resultant slurry, having a mud-like consistency, was dried at 105° C. for about 32 hours in a forced draft oven. The dried cake was broken up and passed through a micronizer equipped with a 0.027 inch screen. About 1,570 grams of the micronized material were thoroughly mixed with an aqueous solution prepared by dissolving about 336 grams of $CuCl_2.2H_2O$ and 136 grams of KCl in 600 milliliters of water. The resultant slurry was dried at 105° C. for about 8 hours and then ground to 40×100 mesh. The catalyst analyzed as follows:

| | |
|---|---|
| Copper (percent by weight) | 6.6 |
| Aluminum (percent by weight) | 4.6 |
| Potassium (percent by weight) | 3.6 |
| Surface Area (square meters per gram) | 17.0 |
| Bulk Density (pounds per cubic foot) | 62.1 |

EXAMPLE 2

An Inconel tube 5 feet in height and 2 inches in diameter was employed as a fluid bed oxyhydrochlorination reactor. The reactor was enclosed in a 6-inch diameter steel jacket forming an annular heat exchange system. "Dowtherm E" (a diphenyl-diphenyloxide eutectic sold by the Dow Chemical Co.) was circulated in the annular space formed between the jacket and the outer surface of the reactor to heat and cool the fluid bed. The reactor was charged to a height of about 25.5 inches with the catalyst composition prepared in Example 1. Ethylene, hydrogen chloride and oxygen were fed at the bottom of the reactor and up through the catalyst bed to maintain the same in a fluidized condition. Reaction temperature ranged from about 280° C. to about 300° C. and contact time between the feed gases and the catalyst bed was about 10 seconds. The gaseous reactants were fed to the reactor in a molar ratio of ethylene to hydrogen chloride to oxygen of 1.0 to 1.5 to 0.45. The crude product gas, exiting from the top of the reactor, was collected, condensed and analyzed. The results and conditions of five test runs utilizing the foregoing procedure are summarized as follows:

| Run No. | 1 | 2 | 3 | 4 | 5 |
|---|---|---|---|---|---|
| Temperature, °C. | 282 | 286 | 290 | 290 | 295 |
| Chloral, weight percent | 0.07 | 0.08 | 0.06 | 0.06 | 0.05 |
| Ethylene dichloride in crude, weight percent | 98.7 | 98.5 | 98.6 | 97.9 | 97.8 |

EXAMPLE 3

About 2,800 grams of 30×60 mesh attapulgite clay were thoroughly mixed with an aqueous solution prepared by dissolving about 1,004 grams of $AlCl_3.6H_2O$, 527 grams of $CuCl_2.2H_2O$ and 213 grams of KCl in 2,250 milliliters of water. The resultant slurry was dried at 105° C. for about 8 hours in a forced draft oven. After drying, the cake was ground to 40×100 mesh and was analyzed as follows:

| | |
|---|---|
| Coper (percent by weight) | 5.1 |
| Aluminum (percent by weight) | 4.8 |
| Potassium (percent by weight) | 2.7 |
| Surface Area (square meters per gram) | 41.0 |
| Bulk Density (pounds per cubic foot) | 50.7 |

EXAMPLE 4

The procedure of Example 2 was followed except that the catalyst composition was that prepared in Example 3. The results of four test runs are summarized as follows:

| Run No. | 1 | 2 | 3 | 4 |
|---|---|---|---|---|
| Temperature, °C. | 275 | 285 | 285 | 295 |
| Chloral, weight percent | 0.13 | 0.19 | 0.18 | 0.09 |
| Ethylene dichloride in crude, weight percent | 99.2 | 98.8 | 99.0 | 98.9 |

EXAMPLE 5

A catalyst composition was prepared following the procedure of Example 3 except that the aluminum chloride was omitted, i.e., the catalyst composition contained only copper chloride and potassium chloride. Using this catalyst composition and following the procedure of Example 2, the ethylene dichloride product was found to contain about 0.5 percent by weight chloral.

EXAMPLE 6

Following the procedure of Example 1, five catalyst compositions containing varying amounts of copper, aluminum and potassium were prepared, which catalyst compositions assayed as follows:

| Composition | A | B | C | D | E |
|---|---|---|---|---|---|
| Cu (weight percent) | 4.5 | 7.5 | 8.4 | 4.6 | 5.9 |
| Al (weight percent) | 6.7 | 6.3 | 6.8 | 6.0 | 5.9 |
| K (weight percent) | 2.4 | 4.1 | 4.4 | 2.4 | 3.1 |
| Surface Area (square meters per gram) | 26 | 29 | 20 | 21 | 16 |
| Bulk Density (pounds per cubic foot) | 47.0 | 50.3 | 57.6 | 55.5 | 47.6 |

EXAMPLE 7

Following the procedure described in Example 2 and using the catalyst compositions prepared in Example 6, the product gas streams analyzed as follows:

| Catalyst Composition | Temperature °C. | Chloral wt. % | Ethylene Dichloride wt. % |
|---|---|---|---|
| A | 285 | 0.03 | 99.1 |
|   | 295 | 0.03 | 99.5 |
| B | 285 | 0.04 | 98.6 |
|   | 295 | 0.04 | 98.2 |
| C | 285 | 0.05 | 98.6 |
|   | 295 | 0.04 | 98.5 |
| D | 285 | 0.07 | 99.1 |
|   | 295 | 0.04 | 98.9 |
| E | 285 | 0.04 | 98.6 |
|   | 295 | 0.04 | 98.8 |

The foregoing clearly demonstrates that the oxyhydrochlorination catalyst of the invention quite effectively reduces to tolerable levels the amount of chloral formed in the oxyhydrochlorination of ethylene to ethylene dichloride. Although the invention has been described with specific references and specific details of embodiments thereof, it is to be understood that it is not intended to be so limited since changes and alterations therein may be made which are within the full intended scope of this invention as defined by the appended claims.

I claim:

1. A catalyst particularly suited for use in the vapor phase oxychlorination of ethylene to produce ethylene dichloride comprising aluminum halide and copper halide carried on a particulate support material wherein aluminum is present in an amount of from 4 to 8 percent by weight and copper is present in an amount of from 4 to 10 percent by weight based on the combined weights of aluminum halide copper halide, and support material.

2. The catalyst of claim 1 wherein the aluminum halide is aluminum chloride and the copper halide is copper chloride.

3. The catalyst of claim 1 wherein copper is present in an amount of from 5 to 8 percent by weight and aluminum is present in an amount of from 5 to 7 percent by weight based on the combined weights of aluminum halide, copper halide and support material.

4. The catalyst of claim 1 wherein the support material is a high silica or alkali metal silicate content clay mineral.

5. The catalyst of claim 4 wherein the particulate support material is an attapulgite clay mineral.

6. The catalyst of claim 1 including alkali metal halide carried on said particulate support.

7. The catalyst of claim 6 wherein the alkali metal halide is sodium chloride or potassium chloride.

8. The catalyst of claim 6 wherein alkali metal is present in an amount of from 2 to 6 percent by weight based on the combined weights of aluminum halide, copper halide, alkali metal halide and support material.

9. A catalyst particularly suited for use in the vapor phase oxychlorination of ethylene to produce ethylene dichloride comprising aluminum halide, copper halide and alkali metal halide carried on a particulate support material wherein aluminum is present in an amount of from 4 to 8 percent by weight, copper is present in an amount of from 4 to 10 percent by weight, and alkali metal is present in an amount of from 2 to 6 percent by weight based on the combined weights of aluminum halide, copper halide, alkali metal halide, and support material.

10. The catalyst of claim 9 wherein aluminum halide is aluminum chloride, copper halide is copper chloride and alkali metal halide is sodium chloride or potassium chloride.

11. The catalyst of claim 9 wherein aluminum is present in an amount of from 5 to 7 percent by weight, copper is present in an amount of from 5 to 8 percent by weight and alkali metal is present in an amount of from 3 to 4 percent by weight based on the combined weights of aluminum halide, copper halide, alkali metal halide and support material.

12. The catalyst of claim 9 wherein the support material is a high silica or alkali metal silicate content clay mineral.

13. The catalyst of claim 12 wherein the support material is an attapulgite clay mineral.

14. A process for preparing a catalyst comprising:
  (a) forming a slurry of a support material in an aqueous solution of aluminum halide;
  (b) drying the aluminum halide treated support material;
  (c) slurrying the dried aluminum halide treated support material in an aqueous solution of copper halide; and
  (d) drying the copper halide treated support material.

15. The process of claim 14 wherein the support material is a high silica or alkali metal silicate content clay mineral.

16. The process of claim 15 wherein the support material is an attapulgite clay mineral.

17. The process of claim 14 wherein sufficient quantities of aluminum halide and copper halide are used such that the catalyst contains from 4 to 8 percent by weight aluminum and from 4 to 10 percent by weight copper based on the combined weights of aluminum halide, copper halide and support material.

18. The process of claim 14 wherein aluminum halide is aluminum chloride and copper halide is copper chloride.

19. The process of claim 14 wherein the aluminum halide solution or the copper chloride solution contain alkali metal halide.

20. The process of claim 19 wherein the alkali metal halide is sodium chloride or potassium chloride.

21. The process of claim 19 wherein a sufficient quantity of alkali metal is used such that the catalyst contains from 2 to 6 percent by weight alkali metal based on the combined weights of aluminum halide, copper halide, alkali metal halide and support material.

* * * * *